United States Patent
McCall et al.

(10) Patent No.: US 9,175,020 B2
(45) Date of Patent: Nov. 3, 2015

(54) PRODUCTION OF LITHIUM DIPHENYLPHOSPHIDE

(75) Inventors: Jeffrey Allen McCall, Kings Mountain, NC (US); Mark J. Hintze, Charlotte, NC (US)

(73) Assignee: Rockwood Lithium Inc., Kings Mountain, NC (US)

( * ) Notice: Subject to any disclaimer, the term of this patent is extended or adjusted under 35 U.S.C. 154(b) by 0 days.

(21) Appl. No.: 12/812,239

(22) PCT Filed: Feb. 13, 2009

(86) PCT No.: PCT/US2009/000936
§ 371 (c)(1),
(2), (4) Date: Jul. 26, 2010

(87) PCT Pub. No.: WO2009/102481
PCT Pub. Date: Aug. 20, 2009

(65) Prior Publication Data
US 2010/0298121 A1    Nov. 25, 2010

(51) Int. Cl.
*B01J 31/12* (2006.01)
*C07F 9/02* (2006.01)
*C01D 15/04* (2006.01)
*C07F 9/50* (2006.01)

(52) U.S. Cl.
CPC . *C07F 9/02* (2013.01); *C01D 15/04* (2013.01); *C07F 9/5022* (2013.01)

(58) Field of Classification Search
None
See application file for complete search history.

(56) References Cited

U.S. PATENT DOCUMENTS

| 4,243,829 | A | * | 1/1981 | Pittman et al. | 585/511 |
| 4,668,795 | A | * | 5/1987 | Andrade et al. | 548/412 |
| 5,677,543 | A | * | 10/1997 | Weiss et al. | 252/182.12 |
| 5,777,169 | A | | 7/1998 | Layman et al. | |
| 5,866,720 | A | | 2/1999 | Layman et al. | |
| 5,892,110 | A | | 4/1999 | Ramprasad et al. | |
| 6,084,133 | A | * | 7/2000 | Kawashima | 568/8 |

FOREIGN PATENT DOCUMENTS

| DE | 259194 A1 | 8/1988 |
| EP | 0 810 028 A2 | 3/1997 |
| JP | 2001-509473 A | 7/2001 |

OTHER PUBLICATIONS

Newkome et al, Chemistry of heterocyclic compounds. 27. An improved preparation of pyridyldiphenylphosphines, 1978, j. org. chem., vol. 43, No. 5 pp. 947-949.*
Hsien et al, Anionic polymerization: principles and practical applications, 1996, pp. 181.*
Boaz et al, Applications of diethoxymethane as verstile preocess solvent and unique reagent in organic synthesis, 2001, organic process research and developement, vol. 5, No. 2 pp. 127-131.*
Aycock, solvent applications of 2 methyltetrafuran in organometallic and biphasic reactions, 2007, organic process reserach and developement, 2007, vol. 11, No. 1 pp. 156-158.*

(Continued)

*Primary Examiner* — Melvin C Mayes
*Assistant Examiner* — Stefanie Cohen
(74) *Attorney, Agent, or Firm* — Norton Rose Fulbright US LLP

(57) ABSTRACT

Lithium diphenylphosphide solutions in a solvent, e.g., diethoxymethane (DEM), that are more stable than when tetrahydrofuran (THF) is used as a solvent. Methods of producing them are also disclosed.

1 Claim, 10 Drawing Sheets

(56) References Cited

OTHER PUBLICATIONS

Reich et al, Solution structure of lithium benzeneselenolate and lithium diphenylphosphide: nmr indentification of cyclic dimers and mixed dimers, 1994, organometallics, ed. 12, pp. 4578-4585.*

Katritzky et al, Transformations of N-Substituted Benzotriazoles into the Corresponding Carbanions by C-Benzotriazole Bond Scission, 1996.*

Fernández, et al. "Li PGSE Doffisopm Measurements on LiPPh2: A Solvent Dependence of the Structure", *Inorganic Chem.* 43 (2004), pp. 4555-4557.

Goldman, et al. "Structure-Reactivity Relationships of Methylated Tetrahydrofurans with Lithium", J. Electrochem. Sty, 126, No. 8 (1979), p. 207C, Abstract XP-001251584.

Goldman, et al. "Structure-Reactivity Relationships of Methylated Tetrahydrofurans with Lithium", J. Electrochem. Sty, 127, No. 7 (1980), pp. 1461-1467.

\* cited by examiner

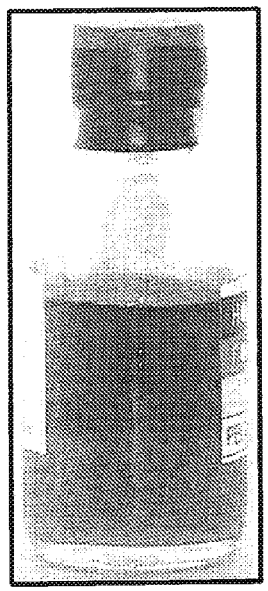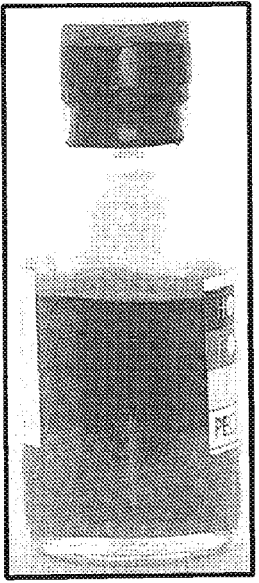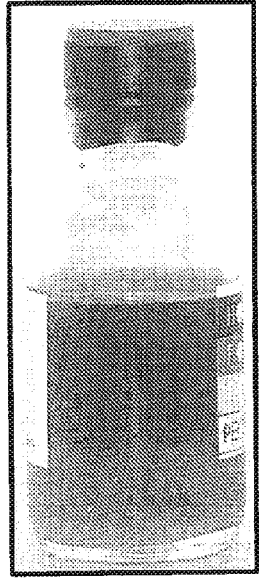
| Day 0 | 20°C 1 Week | 20°C 2 Weeks | 20°C 4 Weeks |
| --- | --- | --- | --- |
| FIG. 13 | FIG. 14 | FIG. 15 | FIG. 16 |
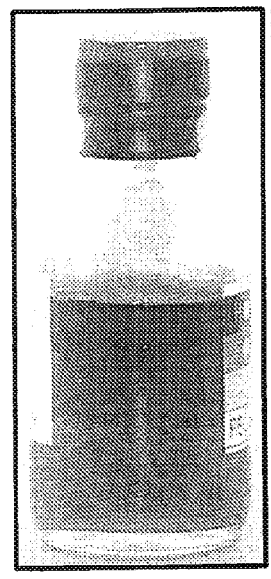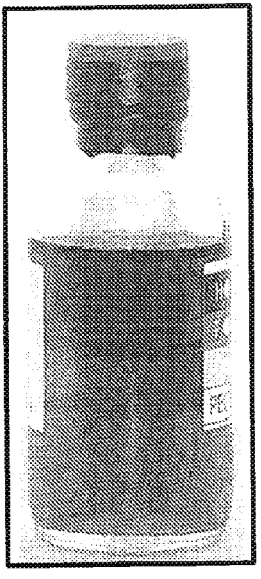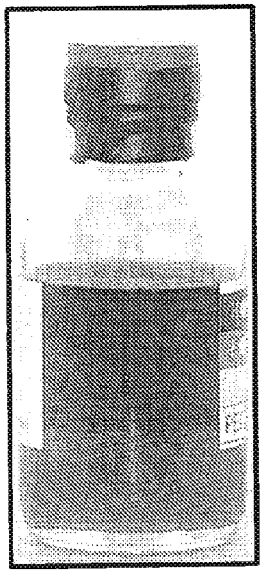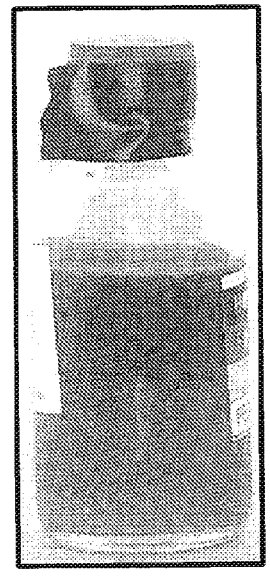
| Day 0 | 35°C 1 Week | 35°C 2 Weeks | 35°C 4 Weeks |
| --- | --- | --- | --- |
| FIG. 17 | FIG. 18 | FIG. 19 | FIG. 20 |

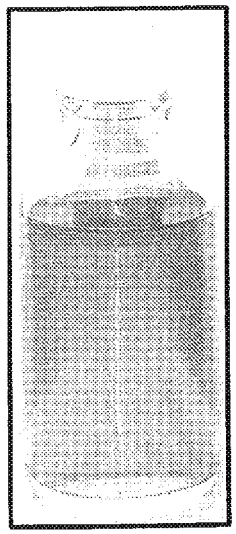 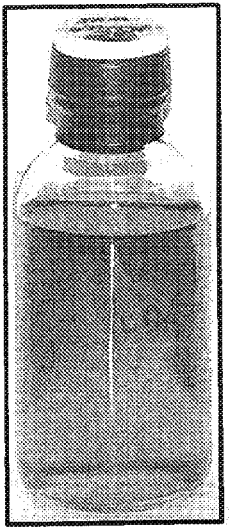 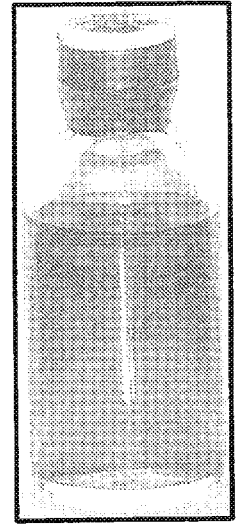 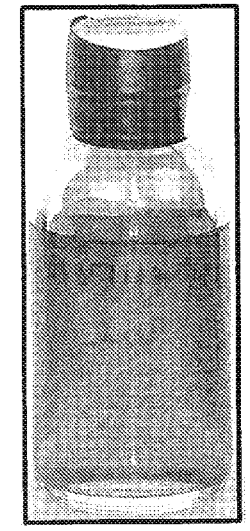
Day 0  20°C 1 Week  20°C 2 Weeks  20°C 4 Weeks
FIG. 21  FIG. 22  FIG. 23  FIG. 24
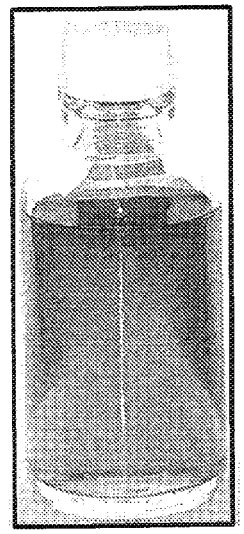 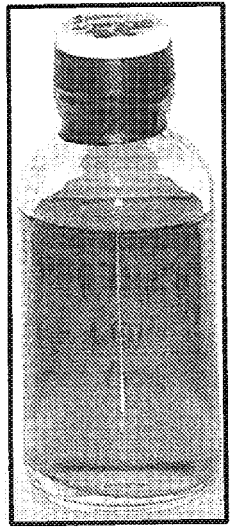 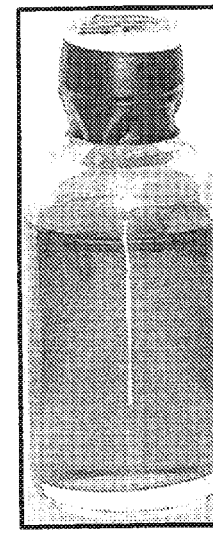 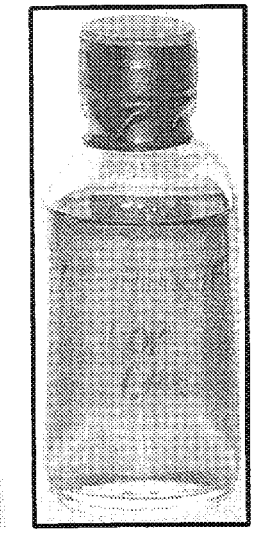
Day 0  35°C 1 Week  35°C 2 Weeks  35°C 4 Weeks
FIG. 25  FIG. 26  FIG. 27  FIG. 28

Day 0

20°C 1 Week

20°C 2 Weeks

20°C 4 Weeks

Day 0

35°C 1 Week

35°C 2 Weeks

35°C 4 Weeks

PRODUCTION OF LITHIUM DIPHENYLPHOSPHIDE

This application is a §371 from PCT/US2009/000936 filed Feb. 13, 2009, which claims the benefit under 35 U.S.C. §119(e) of U.S. Provisional Patent Application Ser. No. 61/029,273 filed Feb. 15, 2008, hereby incorporated by reference in its entirety for all purposes.

FIELD OF THE INVENTION

The present invention relates to lithium diphenylphosphide solutions in a solvent, e.g., diethoxymethane (DEM), that are more stable than when tetrahydrofuran (THF) is used as a solvent, and to methods of producing them.

BACKGROUND OF THE INVENTION

Lithium diphenylphosphide is used commercially to, e.g., to remove a hydroxyl group in organic and in inorganic chemical synthesis or as a ligand in organometallic catalysis. Typically the lithium diphenylphosphide is provided in tetrahydrofuran as a solvent. Such commercially available solutions of lithium diphenylphosphide in tetrahydrofuran are available, but these are not very stable and thus are, not commercially viable. New and stable formulations of diphenylphosphide are necessary.

U.S. Pat. No. 5,866,720 discloses alkali metal diarylphosphides formed by mixing triarylphosphine with, and preferably introducing triarylphosphine into, a two-phase mixture one or more alkali metals, preferably a mixture or alloy of sodium and potassium, in an anhydrous organic liquid diluent in the presence of molecular hydrogen. To form a cycloalkyldiarylphosphine, at least a portion of the reaction mixture as in the aforementioned process (or alkali metal diarylphosphide recovered therefrom) and cycloalkyl mesylate or tosylate are mixed together and maintained under suitable reaction conditions. The latter reaction is driven by the presence of residual sodium from the first reaction. Conduct of the latter reaction under a hydrogen atmosphere suppresses undesirable side reactions.

OBJECTS OF THE INVENTION

Thus, is an object of the present invention to provide stable solutions of diphenylphosphide in solvents such that the solutions are more stable than those in THF. Methods of making and using such solutions are also contemplated to be with in the scope of the present invention. Preferred solvents include ethers, more preferably those with minimal steric hindrance around the oxygen (e.g., $C_1$-$C_5$). Another preferred solvent is 2-methyltetrahydrofuran (2MeTHF), which also yields improved stability, results compared to THF.

SUMMARY OF THE INVENTION

The present invention relates in part to a solution comprising lithium diphenylphosphide and a solvent that yields a more stable solution than when the solution composition is tetrahydrofuran. The stability is preferably improved compared the THF formulations when tested in a controlled atmosphere at 20° C. and at 35° C. in a controlled incubator in an inert positive pressure argon atmosphere for a period of from 1 to 4 weeks, preferably 4 weeks. In preferred embodiments, the solvent contains or is an organic solvent. Preferred solvents include 1 to 5 carbon organics, which preferably contain at least one oxygen atom. Preferred solvents include 2-methyltetrahydrofuran or an ether, e.g., diethyl ether; dimethoxymethane, and triethylorthoformate. Mixtures of solvents are contemplated to be within the scope of the present invention.

Preferred methods for making the compositions of the invention include adding chlorodiphenylphosphine together with lithium metal in a solvent, e.g., such as described above, and reacting to form lithium diphenylphosphide in a solution of the solvent, wherein the solvent yields a more stable solution than when a molar equivalent amount of tetrahydrofuran is used as the solvent. Any amount of THF will, however, decrease the stability of the product.

The reaction is conducted at a temperature of from 30° C. to 80° C.

In preferred embodiments an initiator is added to the solution to promote the formation of diphenylphosphide. A preferred initiator is 1,2-dibromoethane.

BRIEF DESCRIPTION OF THE FIGURES

FIGS. 13-36 are photographs of lithium diphenylphosphide stability sample.

DETAILED DESCRIPTION

Figure 1:
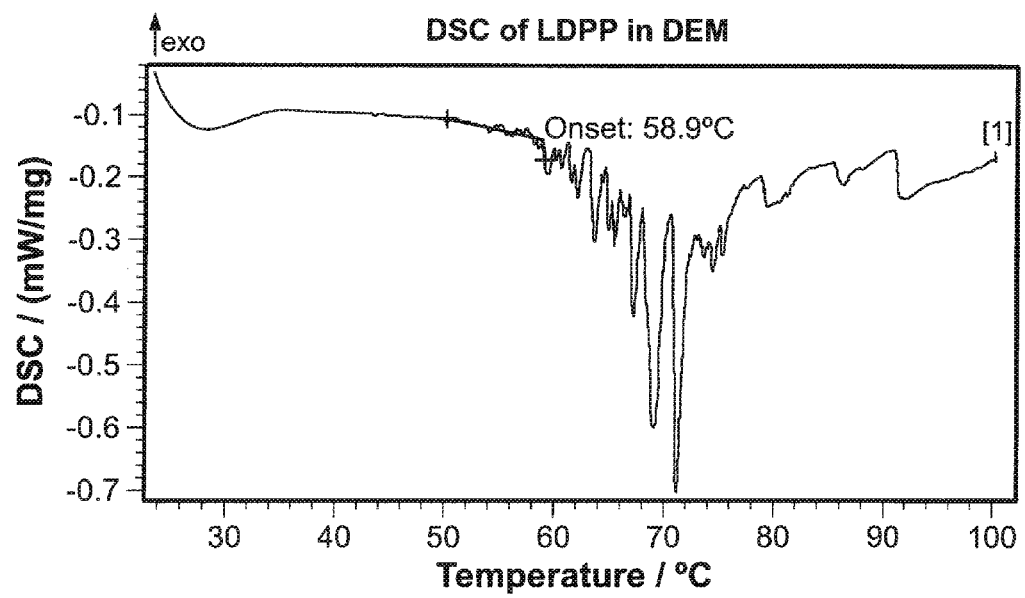
FIG. 1 shows the DSC of LDPP in DEM according to examples 38.
Figure 2:
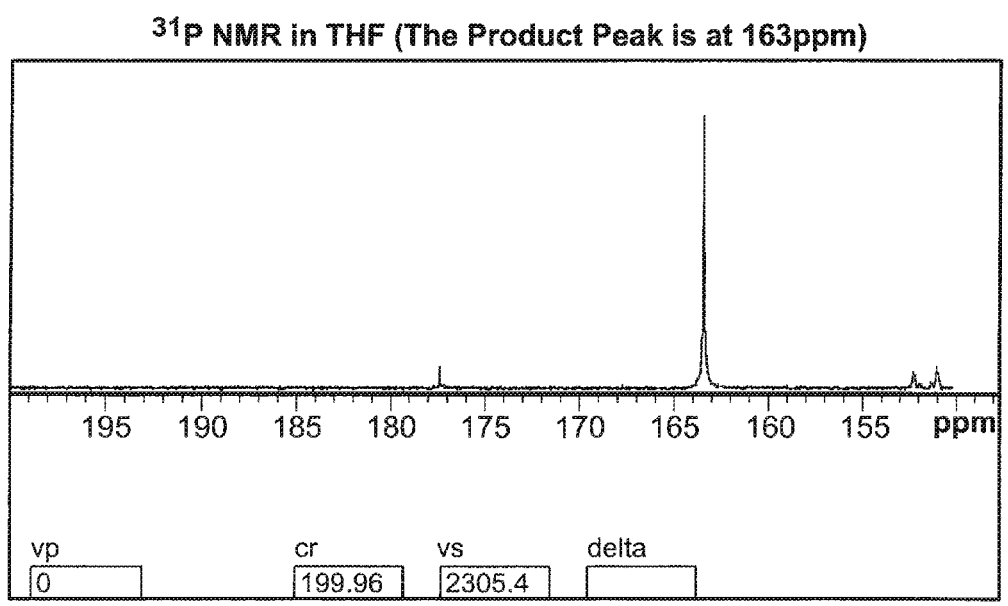
FIGS. 2-12 show NMR spectra for various examples.
Figure 3:
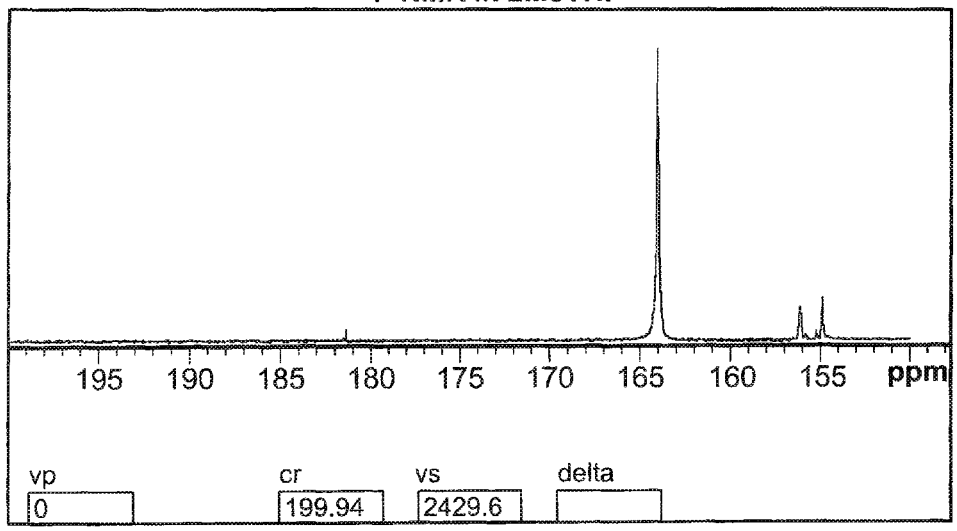
Figure 4:
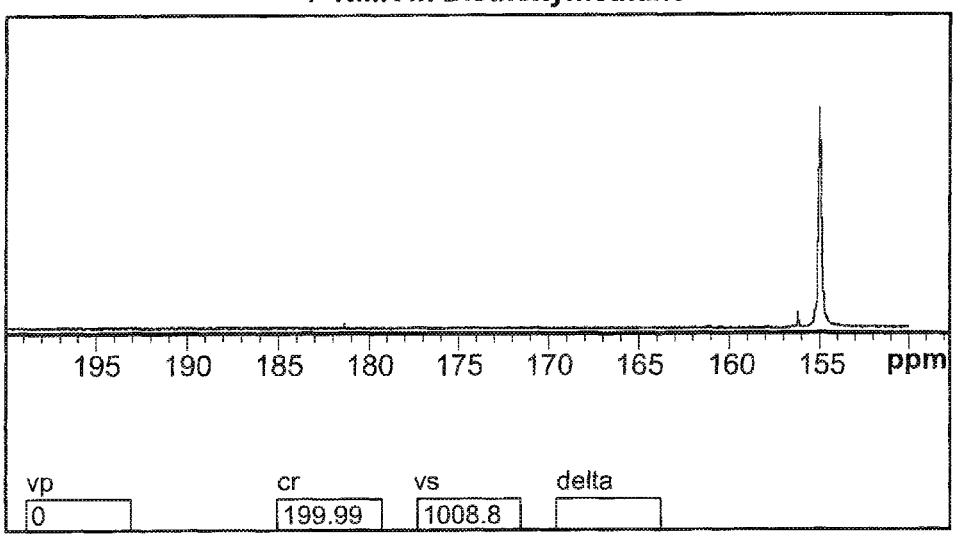
Figure 5:
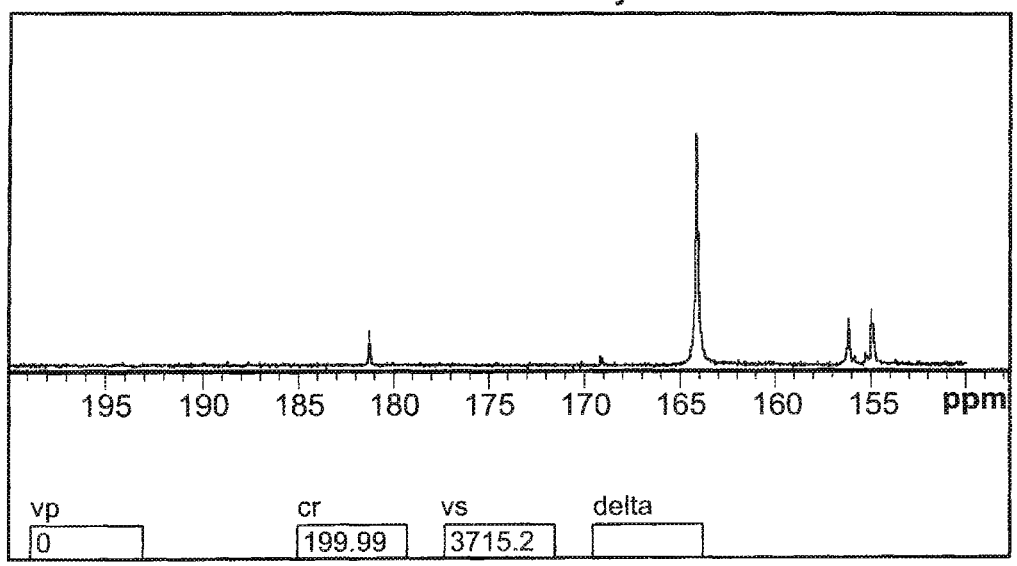
Figure 6:
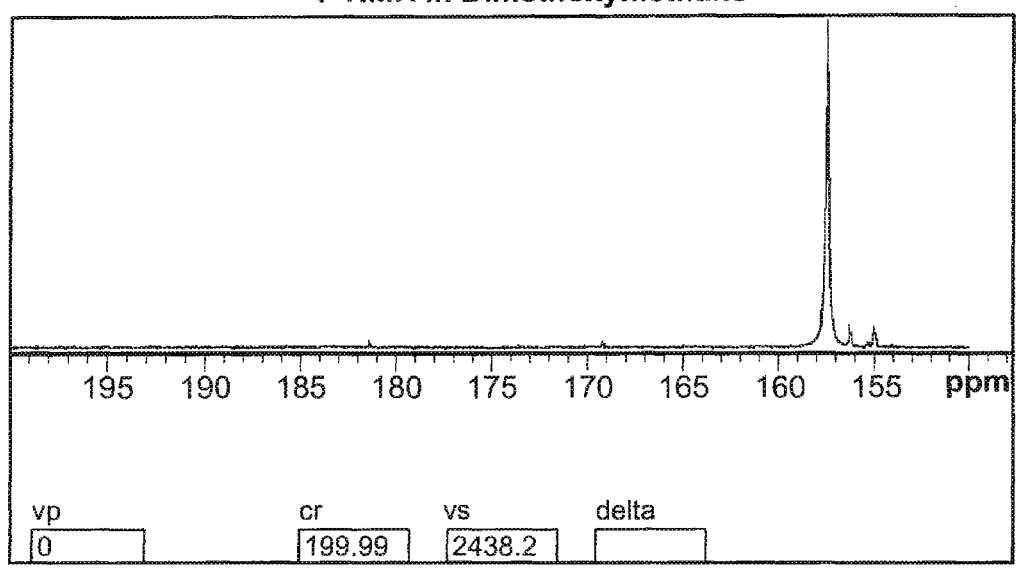
Figure 7:
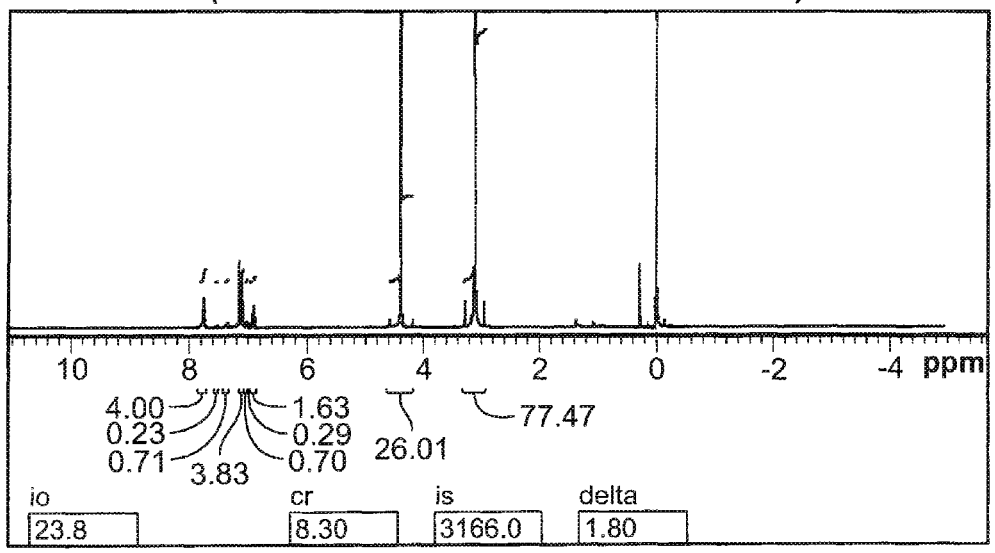
Figure 8:
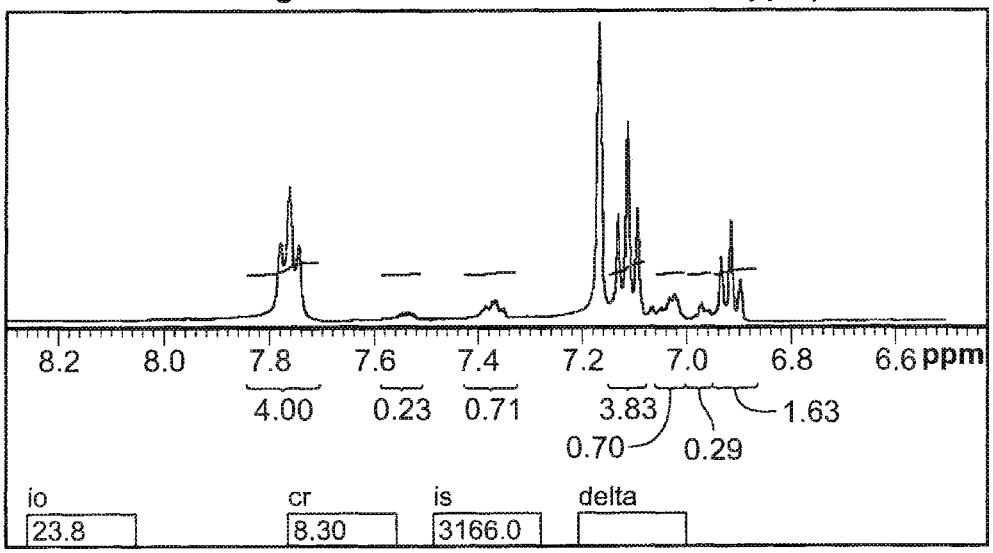
Figure 9:
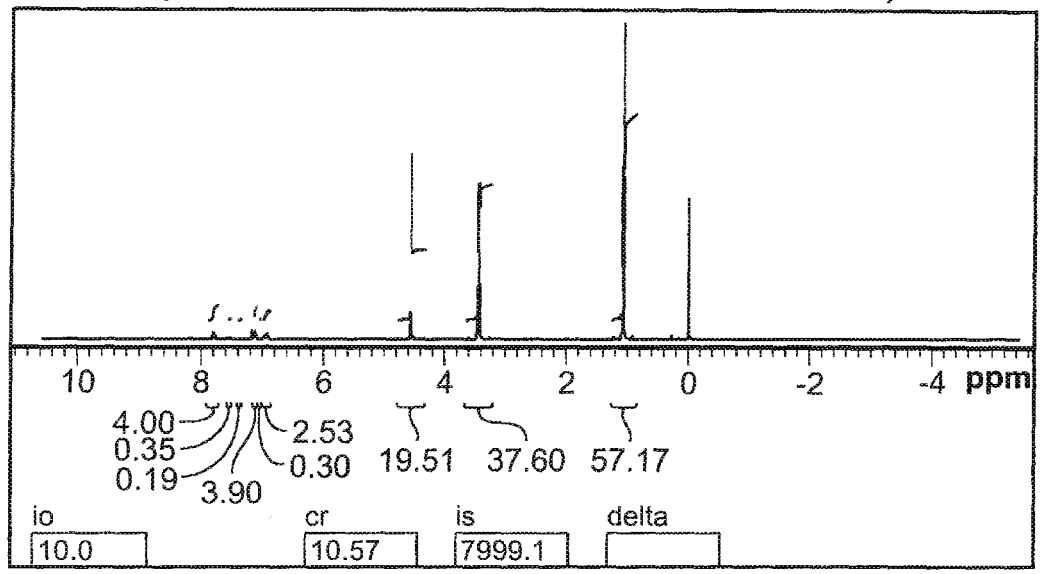

The diphenylphosphide solutions of the invention provide improved stability compared to those in which the solvent is THF. Surprisingly, 2MeTHF shows improved results when used a as solvent, but, broadly, any organic solvent that provides improved stability may be used.

Preferred solvents are $C_1$-$C_5$ compounds, preferably containing oxygen or wherein oxygen substitutes for at least one carbon. When oxygen substitutes for a carbon atom, e.g., in the case of an ether, it is preferred that at least two carbon atoms be present (as in the case of dimethylether). Ethers are a group of preferred solvents, as are furans. Preferred ethers include those that have 1 or 2 ether units (—C—O—C—), and more preferably these are in a straight chain formation. Particularly preferred are diethylether, methylethyl ether and dipropyl ether, thus 6 carbon compounds are also preferred.

A preferred furan is 2MeTHF, which yields improved results compared to its unmethylated counterpart THF.

The lithium metal is preferably pure lithium with little or no impurity, but, more practically, will contain sodium in the range of from 0.001 to 2%, preferably 1.0 to 1.5%, by weight. The lithium metal may be provided in an form, but particularly preferred are lithium metal particles, typically provided as a dispersion in an organic liquid, having an average particle size range of from 1 to 150 microns, preferably 20 to 30 microns. If the lithium metal is provided as a dispersion in a dispersant, e.g., heptane, the dispersant will be removed, e.g., by washing with the solvent of choice to produce the LDPP.

Initiators are any initiator that increases the initial rate of reaction of the starting p-chlorodiphenylphosphine and lithium to lithium diphenylphosphide. A preferred initiator is 1,2-dibromoethane.

In a preferred embodiment, the lithium, the solvent and the p-chlorodiphenylphosphine are added together and reacted at a temperature of from 30° C. to 80° C., preferably from 30° C. to 40° C., or from greater than 40° C. to 80° C. The temperature is preferably less than 50° C. as the product may decompose at or above this temperature.

The reactants may be mixed in any order, but it is preferred to add the lithium metal to the solvent before adding the p-chlorodiphenylphosphine The reaction should be run for a suitable period of time to finish the reaction, preferably from 1 minute to 10 hours, more preferably from 20 minutes to 5 hours.

The resultant lithium diphenylphosphide is recovered by any suitable means, e.g., by filtration. Lower temperatures improve the time necessary for filtration.

Preferred embodiments of the products and methods of the invention are described in the examples that follow.

DESCRIPTION OF PREFERRED EMBODIMENTS

Example 1

Reagents:

Lithium (tech grade metal from Chemetall Foote, New Johnsonville, (containing about 1% sodium as an impurity in the metal having an average particle size of from 20-30 microns) stored in heptane was redispersed and rinsed with hexane and dried with argon. The dried dispersed metal was mixed 1:0.5 wt/wt with mineral oil and stored in a glovebox. Mineral oil is added to the lithium dispersion to prevent the dried metal from becoming airborne in the glove box. Sodium was not added to this metal beyond what was contained.

p-Chlorodiphenylphosphine commercially available from Aldrich (St. Louis, Mo.) (cat# C39601, 98%) was used as received.

Solvents tested include tetrahydrofuran (for comparison), diethyl ether and 2MeTHF. These were distilled over sodium metal prior to use to dry the solvent. Other solvents were either dried with molecular sieves or tested for moisture prior to use. No purification was performed prior to use.

Equipment:

Unless otherwise noted all reactions were run in a glass round-bottom flask and stirred with a Teflon coated stir bar. All reactions were kept under argon with positive pressure maintained by using a mineral oil bubbler. For smaller reactions (70 ml) the chlorodiphenylphosphine was added to the flask with a syringe fitted with a long stainless steel needle. The rate was controlled by a syringe pump.

For the larger reactions (700 mL) the p-chlorodiphenylphosphine was added via a pressure equalizing addition funnel and the addition rate was varied to keep the correct reaction temperature.

Reactions were cooled to maintain a temperature at or below 40° C., if necessary. Temperature was measured with a glass thermometer. The small scale reactions were filtered through a glass frit filter (25-50 μm) and the larger reactions were filtered through a stainless steel filter housing (3" diameter) with a polypropylene filter cloth. Both filters used Eagle-Picher Celatom FW-12 filter aid as a filter bed.

NMR spectra were taken on a Varian 400MR using deuterated benzene as the solvent and the proton spectra were referenced to tetramethylsilane. The phosphorous spectra were uncorrected (i.e., no internal standard to set the ppm scale).

Example Reaction in DEM:

$$2Li + Ph_2PCl \xrightarrow{DEM} Ph_2PLi + LiCl$$

Amounts used in this experiment:
Lithium: 9.57 g (1.38 mol)
Chlorodiphenylphosphine: 126.22 g (0.572 mol)
Diethoxymethane: 489.12 g Lithium (as described above, 1:0.5 in mineral oil) was charged to a 1 liter flask equipped with a stir bar. The flask was fitted with a thermometer and an addition funnel. The DEM was added and the stirring was started. Approximately 10% (10 mL) of the starting material was added to the flask. Three hours later the temperature had risen 21° C. and the addition was begun. The temperature was maintained at 30° C. t 2° C. by cooling, if necessary. The addition took 80 minutes. After 1.5 hours an NMR spectra was taken and showed that the reaction was incomplete, so the solution was stirred overnight. The following morning the reaction was finished. The solution was then filtered to recover the lithium diphenylphosphine, and the filter cake was then rinsed with 16.442 g of DEM. 601.96 g of clear brown solution was collected and a sample was submitted to analytical (active: 17.91%, yield: 98.09%).

Table 1 (below) lists solvents that were tested as well as yields obtained. The reactions to make the lithium diphenylphosphide were run at temperatures ranging from 30° C. to 80° C. Data showed that conducting the reaction at a temperature ≤40° C. improved the yield and decreased the filtration time, and this is a preferred embodiment of the present invention. Running the reaction at higher temperatures led to a filtration time of approximately 3 hours, while when conducted at 30° C.-40° C. filtration time was reduced to only 30-60 minutes. From the differential scanning calorimetry (DSC) plot (FIG. 1) it can be seen that the product starts to decompose at approximately 50° C.

Initiation of the reaction on small scale (70 mL) took 10-20 minutes. However, on larger scale (700 mL) the initiation could take up to 3 hours.

Addition of a starter solution of the lithium diphenylphosphide to the flask was shown to allow the reaction to initiate quickly, but this is not necessary to practice the invention, although it is a preferred embodiment.

1,2-dibromoethane was also added in Example 37 (4.2 gm) and shown to decrease time necessary for initiation on large scale experiments (700 mL) to approximately 1 hour.

Figure 10:
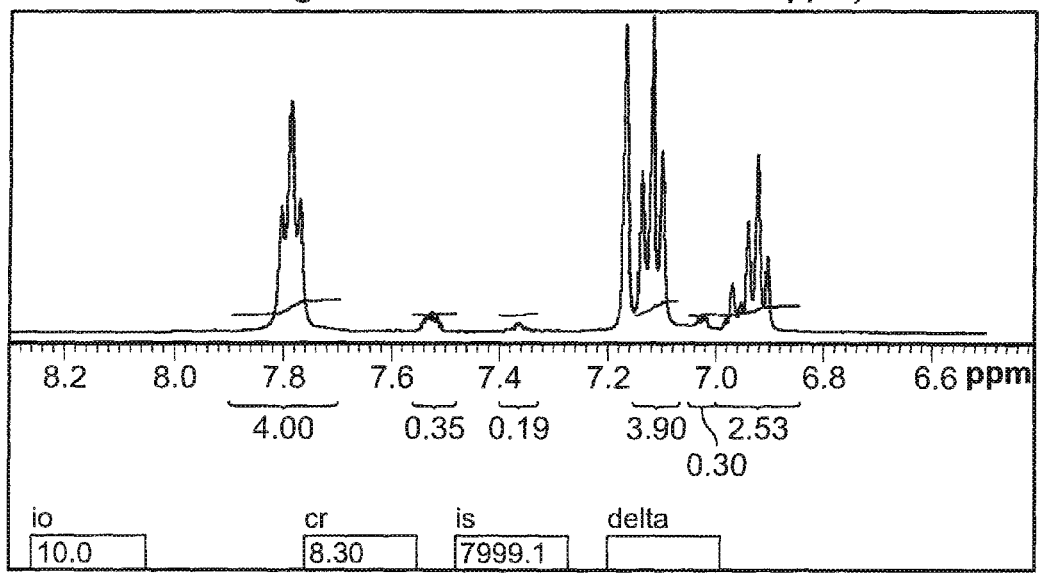
Figure 11:
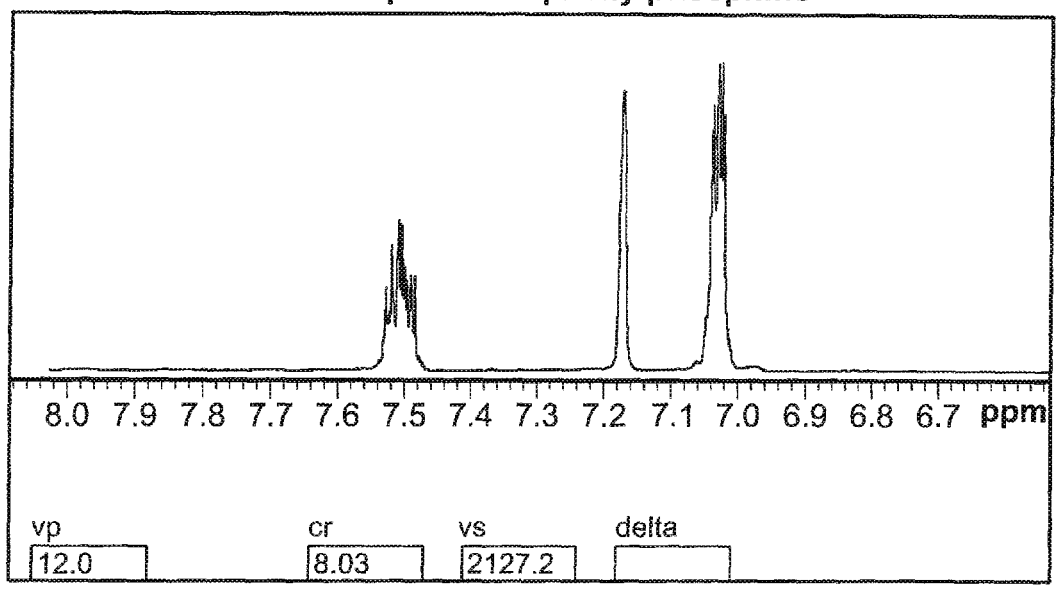
Figure 12:
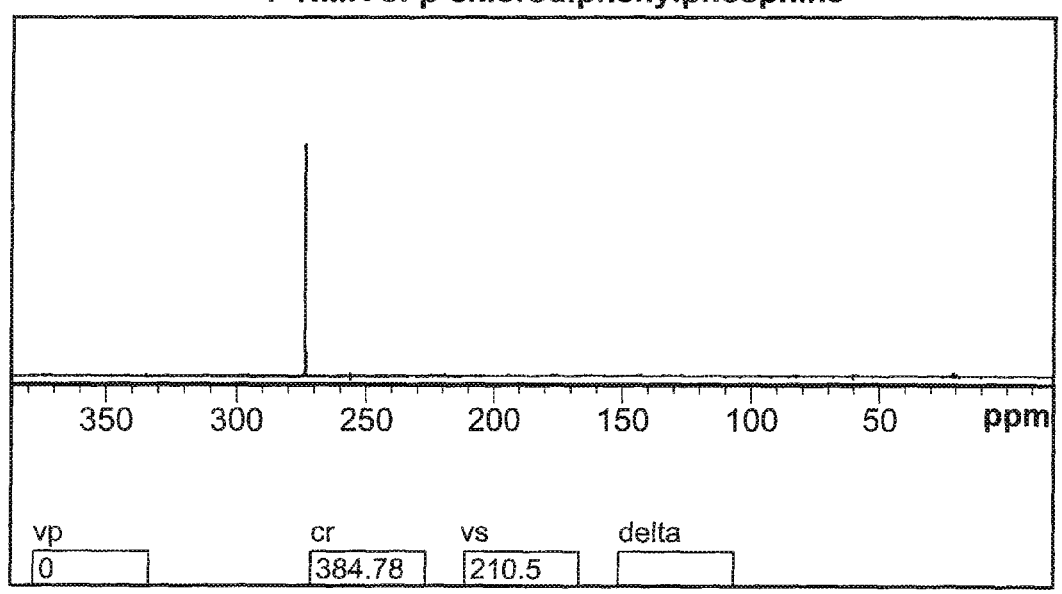
Figure 29:
Figure 30:
Figure 31:
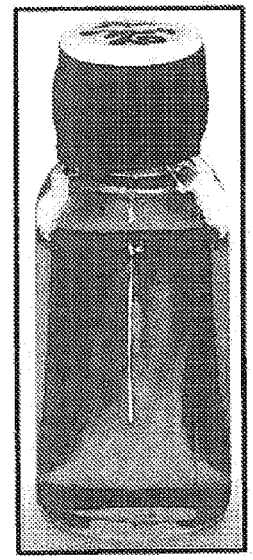
Figure 32:
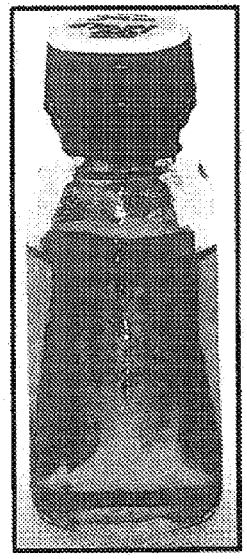
Figure 33:
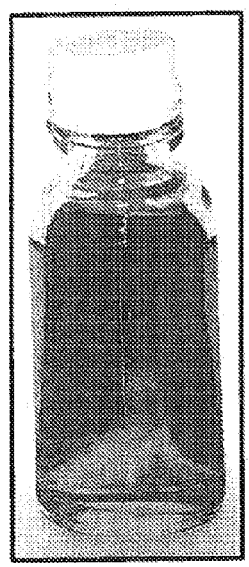
Figure 34:
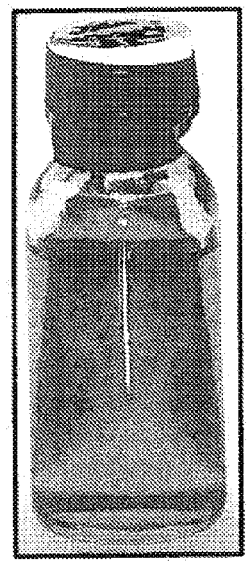
Figure 35:
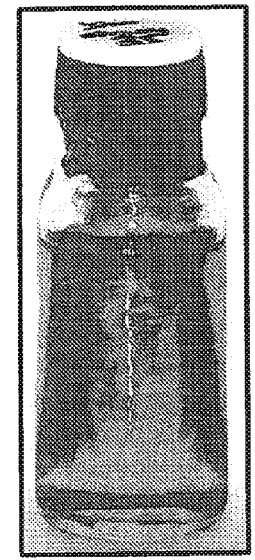
Figure 36:

Progress of the reactions were monitored by both temperature and NMR. When starting a reaction an increase in temperature along with a solution color change to green indicated that the reaction had started. To check the progress of the reaction NMR samples were taken and the peaks in the aromatic region were compared (FIGS. 10 and 11).

Stability for this product was tested at 20° C. and 35° C. in a controlled temperature incubator in an inert positive pressure argon atmosphere (see Tables 2-9). Samples were placed into 2 ounce glass bottles having Teflon caps and were stored at these temperatures for up to 4 weeks. Example 28 had a larger than usual amount of starting material remaining in the solution at the end of the reaction (ratio of 4:1 product to starting material as opposed to a typical ratio of 4:0.3). By the 4 week stability test the samples had developed a film that formed on the walls of the glass bottles. This film was not seen in any other samples.

Titration Set-Up.

Figure 37:
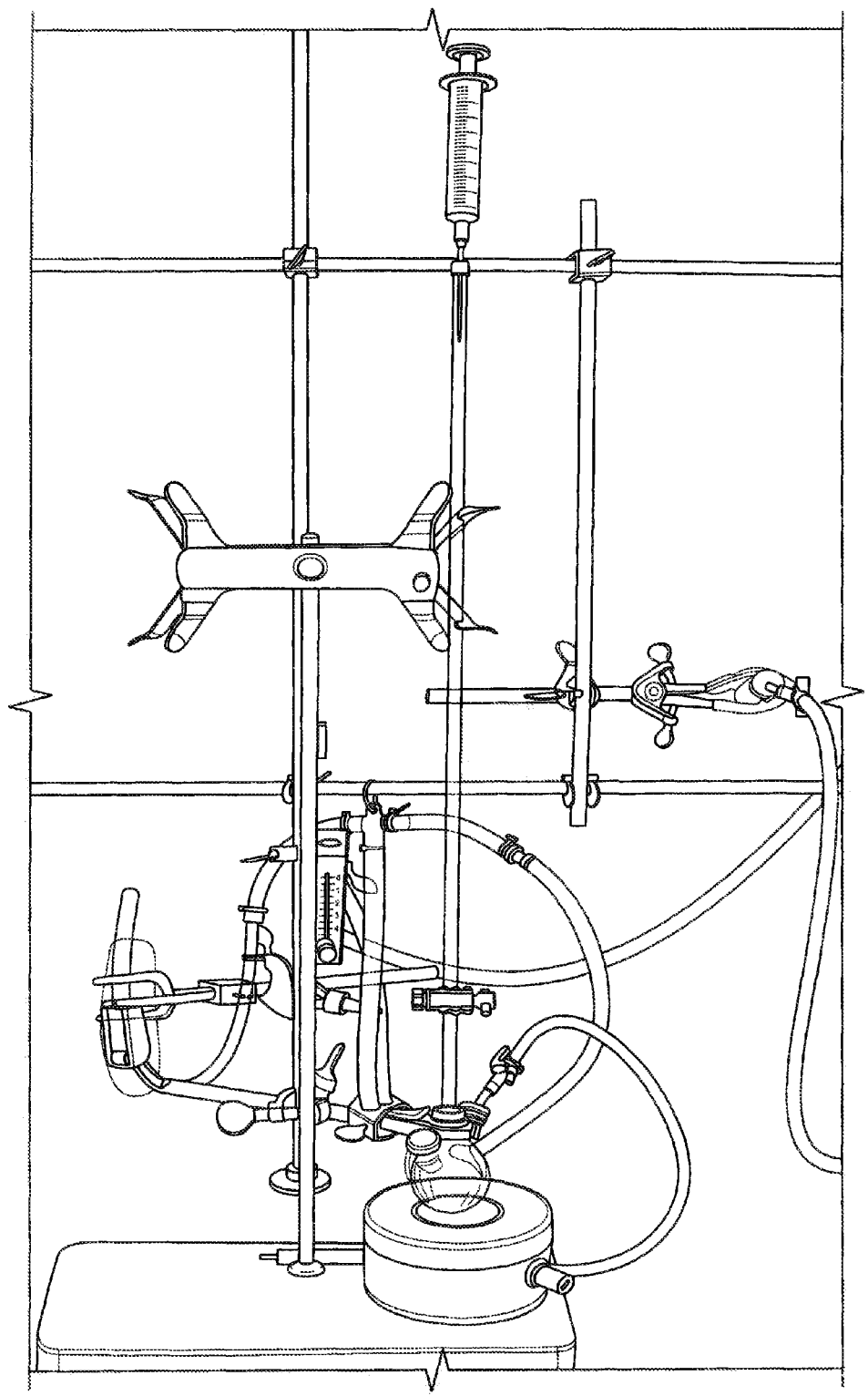
FIG. 37 show an apparatus used in titration of samples prepared according to the examples.

A dried, argon purged, 3-neck roundbottom flask was capped with septa and kept under an argon atmosphere with an argon line. The dried burette was cooled, capped with a septa, and the tip was introduced into the roundbottom flask through a hole in the septa (see FIG. 37) A glass syringe full

TABLE 1

DATA FOR EXAMPLES 1-42

| Example | Li g | CDP g | Li/CDP | solvent Type | solvent g | Temp C. | Active % | Yield % |
|---|---|---|---|---|---|---|---|---|
| 1 | 0.91 | 13.282 | 1.09 | THF | 60.81 | 40 | 9.2 | 60.23 |
| 2 | 0.94 | 13.203 | 1.13 | THF | 61.45 | 50 | 15.04 | 93.65 |
| 3 | 0.933 | 13.291 | 1.12 | THF | 61.29 | 49 | 13.16 | 86.91 |
| 4 | 0.91 | 13.344 | 1.08 | THF | 60.26 | 56 | 13.21 | 83.89 |
| 5 | 1.01 | 13.419 | 1.20 | THF | 59.78 | 65 | 14.28 | 90.84 |
| 6 | 0.647 | 9.105 | 1.13 | THF | 59.99 | 56 | 11.14 | 99.78 |
| 7 | 7.233 | 99.66 | 1.15 | THF | 498.4 | 62 | 13.9 | 94.75 |
| 8 | 7.4 | 100.08 | 1.18 | THF | 503.81 | 62 | 14.06 | 96.79 |
| 9 | 1.62 | 22.867 | 1.13 | THF | 61.48 | 60 | 21.58 | 92.36 |
| 10 | 2.19 | 30.244 | 1.15 | THF | 50.36 | 67 | 29.27 | 88.02 |
| 11 | 0.907 | NA | | THF/hexane | 8.78/51.40 | 55 | na | na |
| 12 | 0.94 | 13.408 | 1.11 | dibutylether | 53.27 | 64 | 9.02 | 48.43 |
| 13 | 0.953 | 13.169 | 1.15 | DEM | 59.98 | 65 | 14.9 | 93.26 |
| 14 | 0.94 | 13.046 | 1.15 | DEM | 57.91 | 70 | 14.81 | 85.94 |
| 15 | 0.947 | 13.179 | 1.14 | DEM | 51.7 | 50 | 16.58 | 90.95 |
| 16 | 0.94 | 13.079 | 1.14 | DEM | 52.72 | 52 | 16.36 | 92.21 |
| 17 | 0.93 | 13.097 | 1.13 | DEM | 52.89 | 68 | 15.76 | 88.12 |
| 18 | 0.93 | 13.313 | 1.11 | MTBE | 52.26 | 48 | nr | nr |
| 19 | 0.927 | 13.163 | 1.12 | 2MeTHF | 52.66 | 51 | 15.8 | 89.35 |
| 20 | 0.92 | 13.171 | 1.11 | DME | 52.19 | 50 | 10.41 | 53 |
| 21 | 0.913 | | | isopropylether | 51.94 | | nr | Nr |
| 22 | 0.933 | 13.234 | 1.12 | DMM | 50.78 | 42 | 14.5 | 73.47 |
| 23 | 0.913 | 13.363 | 1.09 | Ether | 53.85 | 34 | 14.25 | 75.35 |
| 24 | 0.94 | 13.082 | 1.14 | DME | 53.15 | 50 | 13.32 | 75.93 |
| 25 | 0.94 | 13.204 | 1.1316 | TEOF | 51.48 | 51 | 12.84 | 68.59 |
| 26 | 0.92 | 13.17 | 1.1104 | DEM | 51.7 | 52 | 16.32 | 89.44 |
| 27 | 0.92 | 13.315 | 1.0983 | Ether | 52.31 | 34 | 17.32 | 89.92 |
| 28 | 8.733 | 124.74 | 1.1128 | DEM | 479.384 | 60 | 15.53 | 78.71 |
| 29 | 8.72 | 121.69 | 1.139 | DEM | 469.1 | 60 | 17.44 | 92.4 |
| 30 | 9.47 | 122.73 | 1.2265 | 2MeTHF | 466.69 | 80 | 15.26 | 76.6 |
| 31 | 9.827 | 122.93 | 1.2707 | DEM | 475.56 | 78 | 16.47 | 83.63 |
| 32 | 0.92 | 13.44 | 1.0881 | DEM | 51.89 | 31 | 16.76 | 89.87 |
| 33 | 1.04 | 13.179 | 1.2544 | DEM | 51.87 | 31 | 17.2 | 94.16 |
| 34 | 9.57 | 126.22 | 1.2052 | DEM | 489.12 | 31 | 17.91 | 98.09 |
| 35 | 1.01 | 13.33 | 1.2044 | DEM | 51.25 | 31 | 17.82 | 95.42 |
| 36 | 9.693 | 122.62 | 1.2565 | DEM | 471.24 | 31 | 17.19 | 94.74 |
| 37 | 9.51 | 124.19 | 1.2172 | DEM | 493.97 | 31 | 17.34 | 94.97 |
| 38 | 1.013 | 13.219 | 1.2181 | DEM | 51.18 | 41 | 17.96 | 96.56 |
| 39 | 19.17 | 250.47 | 1.2166 | DEM | 720.68 | 31 | 22.35 | 98.25 |
| 40 | 19.17 | 259.78 | 1.1729 | DEM | 721.94 | 30 | 21.1 | 91.14 |
| 41 | 19.06 | 251.2 | 1.2061 | DEM | 717.43 | 31 | 22.01 | 99.52 |
| 42 | 11.94 | 155.81 | 1.2181 | DEM | 434.45 | 32 | 20.9 | 93.84 | nr = no reaction
TEOF = triethylorthoformate
THF = tetrahydrofuran
DEM = diethoxymethane
DMM = dimethoxymethane
2MeTHF = 2 methyl tetrahydrofuran
ether = diethylether
NA = In Example 11, NA means that the product formed but crystallized out of solution rather than forming a dispersion The following is the methodology used to calculate the data in Table 1:

Determination of Active Base in Lithium Diphenylphosphide (LDPP) by Titration with Sec-Butanol General.

All glassware should be oven dried and purged with argon. The xylenes and sec-butanol were dried over activated molecular sieves prior to use. The titration was done under an inert atmosphere of dry argon.

of argon was put through the septa at the top of the burette to equalize the pressure during the titration.

Solvent Preparation and Drying.

An argon purged syringe was used to transfer 20 ml of xylenes to the round bottom flask. An argon purged syringe was used to transfer 0.5 ml of a 0.05M 1,10-phenanthroline indicator solution in xylenes to the flask. Another purged syringe with needle was used to add a few drops of the sample to the solution in the flask until the color changes to a dark purple. The sample in the flask was titrated with a 0.5M sec-butanol in xylenes titrant until the indicator endpoint was reached. The volume was record on the burette as the starting volume.

Titration.

An argon purged syringe with needle was used to draw a 2 mL sample and the weight of the sample was recorded to the nearest 0.0001 gram as $wgt_{sample}$. The sample was injected into the titration flask and was titrated to the indicator endpoint. The final volume was recorded and the volume used was calculated during the titration. The volume of titrant used was calculated as $V_{titrant}$, in liters.

Active Base Concentration $$wgt\ \% = 100\% * V_{titrant} * M_{sec-butanol} * MW_{sample} / wgt_{sample}$$

Stability

Several solutions of LDPP in various solvents were tested for stability. The results are shown in the tables below. The samples that do not list temperatures were conducted at 20° C. and the analyses were run on the same sample. The samples that do list temperatures had multiple samples from the same batch. All data shown in wt. %.

TABLE 2

Stability of LDPP in tetrahydrofuran
LDPP in THF

|  |  | Week 1 | | Week 2 | | Week 4 | |
| --- | --- | --- | --- | --- | --- | --- | --- |
| Ex. 19 | Day 0 | 20 C. | 35 C. | 20 C. | 35 C. | 20 C. | 35 C. |
| Active | 11.08 | 10.1 | 8.8 | 9.23 | 4.58 | 7.62 | 1 |
| Total | 11.97 | 12 | 12 | 12.02 | 12.04 | 12.01 | 12.04 |

TABLE 3

Stability of LDPP in diethoxymethane
LDPP in DEM

| Ex. 13 | Day 0 | Week 1 | Week 2 | Week 4 |
| --- | --- | --- | --- | --- |
| Active | 14.9 | 14.56 | 14.54 | 14.52 |
| Total | 15.5 | 15.56 | 15.66 | 15.65 |

TABLE 4

Stability of LDPP in 2-methyltetrahydrofuran
LDPP in 2MeTHF

| Ex. 19 | Day 0 | Week 1 | Week 2 | Week 4 |
| --- | --- | --- | --- | --- |
| Active | 15.8 | 15.5 | 15.48 | 15.42 |
| Total | 16.06 | 16.17 | 16.21 | 16.24 |

TABLE 5

Stability of LDPP in ether
LDPP in ether

| Ex. 23 | Day 0 | Week 1 | Week 2 | Week 4 |
| --- | --- | --- | --- | --- |
| Active | 14.28 | 14.06 | 14.04 | 14.04 |
| Total | 15.54 | 15.56 | 15.54 | 15.55 |

TABLE 6

Stability of LDPP in triethylorthoformate.
LDPP in triethyl orthoformate

| Ex. 25 | Day 0 | Week 1 | Week 2 | Week 4 |
| --- | --- | --- | --- | --- |
| Active | 12.84 | 10.96 | 8.98 | 6.34 |
| Total | 13.03 | 13.04 | 12.985 | 12.99 |

TABLE 7

Stability of LDPP in diethoxymethane
LDPP in DEM

|  |  | Week 1 | | Week 2 | | Week 4 | |
| --- | --- | --- | --- | --- | --- | --- | --- |
| Ex. 28 | Day 0 | 20 C. | 35 C. | 20 C. | 35 C. | 20 C. | 35 C |
| Active | 15.53 | 15.54 | 15.44 | 15.52 | 15.25 | 15.48 | 14.88 |
| Total | 17.1 | 17.11 | 17.13 | 17.08 | 17.1 | 17.03 | 16.96 |

TABLE 8

Stability of LDPP in diethoxymethane
LDPP in DEM

|  |  | Week 1 | | Week 2 | | Week 4 | |
| --- | --- | --- | --- | --- | --- | --- | --- |
| Ex. 29 | Day 0 | 20 C. | 35 C. | 20 C. | 35 C. | 20 C. | 35 C. |
| Active | 17.44 | 17.42 | 17.36 | 17.41 | 17.26 | 17.39 | 17.12 |
| Total | 18.03 | 18.02 | 18.01 | 18.06 | 18.09 | 18.04 | 18.06 |

TABLE 9

Stability of LDPP in 2MeTHF.
LDPP in 2MeTHF

|  |  | Week 1 | | Week 2 | | Week 4 | |
| --- | --- | --- | --- | --- | --- | --- | --- |
| Ex. 30 | Day 0 | 20 C. | 35 C. | 20 C. | 35 C. | 20 C. | 35 C. |
| Active | 15.26 | 15.18 | 14.80 | 15.16 | 14.59 | 15.13 | 14.39 |
| Total | 15.64 | 15.66 | 15.66 | 15.62 | 15.66 | 15.38 | 15.64 |

The results show that improved and stable lithium diphenylphosphide formulations can be prepared using solvents other than THF. With the exception of triethylorthoformate, all of the solvents used in the experiments above showed improved results compared to the THF formulations.

All references cited herein are incorporated by reference in their entireties for all purposes.

It is claimed:

1. A solution comprising lithium diphenylphosphide, an initiator, and a solvent that yields a more stable solution than when the solution contains tetrahydrofuran as a solvent, wherein the solvent comprises dimethoxymethane.

* * * * *